United States Patent
Hansmann et al.

(10) Patent No.: US 9,759,702 B2
(45) Date of Patent: Sep. 12, 2017

(54) REACTION CARRIER, MEASURING SYSTEM AND MEASURING METHOD FOR DETERMINING GAS AND PARTICLE CONCENTRATIONS, AND OPTICAL FLOW SENSOR

(71) Applicant: Dräger Safety AG & Co. KGaA, Lübeck (DE)

(72) Inventors: Hans-Ullrich Hansmann, Barnitz (DE); Philipp Rostalski, Lübeck (DE)

(73) Assignee: DRÄGER SAFETY AG & CO. KGAA, Lübeck (DE)

( * ) Notice: Subject to any disclaimer, the term of this patent is extended or adjusted under 35 U.S.C. 154(b) by 0 days.

(21) Appl. No.: 14/896,785

(22) PCT Filed: May 20, 2014

(86) PCT No.: PCT/EP2014/001351
§ 371 (c)(1),
(2) Date: Dec. 8, 2015

(87) PCT Pub. No.: WO2014/194983
PCT Pub. Date: Dec. 11, 2014

(65) Prior Publication Data
US 2016/0131627 A1 May 12, 2016

(30) Foreign Application Priority Data
Jun. 8, 2013 (DE) .................. 10 2013 009 642

(51) Int. Cl.
*G01N 15/06* (2006.01)
*G01N 33/00* (2006.01)
(Continued)

(52) U.S. Cl.
CPC ......... *G01N 33/0067* (2013.01); *G01F 1/661* (2013.01); *G01F 1/704* (2013.01);
(Continued)

(58) Field of Classification Search
CPC ......... G01N 15/06; G01N 33/00; G01N 33/48
(Continued)

(56) References Cited

U.S. PATENT DOCUMENTS 4,123,227 A  10/1978  Heim et al.
4,245,997 A   1/1981  Wiesner
(Continued)

FOREIGN PATENT DOCUMENTS

DE  26 28 790 B1  11/1977
DE  28 14 843 B1   8/1979
(Continued)

*Primary Examiner* — Brian J Sines
(74) *Attorney, Agent, or Firm* — McGlew and Tuttle, P.C.

(57) ABSTRACT

A measuring system (10) and method measure a concentration of components of a gas mixture of gas/aerosol. A reaction support (14) has a flow channel (42) that forms a reaction chamber (46) with an optically detectable reactant (48) that reacts with at least one component or with a reaction product of the component. The flow channel (42) is at least partially filled with particles (100, 102, 104, 110) which have a pre-flow starting position and to which a gas flow is applied through the flow channel (42) in a flow position. The particles (100, 102, 104, 110) are designed (configured) in such a manner that the particles (100, 102, 104, 110) in the starting position and the particles (100, 102, 104, 110) in the flow position can be optically distinguished. The invention also relates to an optical flow sensor (109) for determining a flow of a fluid.

20 Claims, 8 Drawing Sheets

(51) Int. Cl.
*G01N 33/48* (2006.01)
*G01P 5/00* (2006.01)
*G01F 1/66* (2006.01)
*G01F 1/704* (2006.01)
*G01P 5/20* (2006.01)
*G01F 1/708* (2006.01)
*G01N 21/77* (2006.01)
*G01N 21/85* (2006.01)
*G01F 1/74* (2006.01)
*G01N 15/00* (2006.01)
*G01N 31/22* (2006.01)

(52) U.S. Cl.
CPC ........... *G01F 1/7086* (2013.01); *G01N 21/77* (2013.01); *G01N 21/85* (2013.01); *G01N 33/007* (2013.01); *G01P 5/001* (2013.01); *G01P 5/20* (2013.01); *G01F 1/74* (2013.01); *G01N 31/223* (2013.01); *G01N 2015/0026* (2013.01)

(58) Field of Classification Search
USPC ........... 422/68.1, 82.01, 83, 98; 436/43, 164
See application file for complete search history.

(56) References Cited

U.S. PATENT DOCUMENTS

| 2001/0031224 | A1 | 10/2001 | Labuda et al. |
| 2002/0060292 | A1* | 5/2002 | Namose et al. ......... 250/339.09 |
| 2004/0267151 | A1* | 12/2004 | Eckerbom ................... 600/532 |
| 2011/0228276 | A1 | 9/2011 | Hiranaka et al. |
| 2013/0088716 | A1 | 4/2013 | Romanin et al. |

FOREIGN PATENT DOCUMENTS

| DE | 13 03 861 A1 | 8/1994 |
| DE | 10 2008 041 330 A1 | 2/2010 |
| DE | 10 2010 040717 A1 | 4/2012 |
| DE | 10 2012 014 503 A1 | 1/2014 |
| EP | 1 983 340 A1 | 10/2008 |
| EP | 2 405 254 A1 | 1/2012 |

* cited by examiner

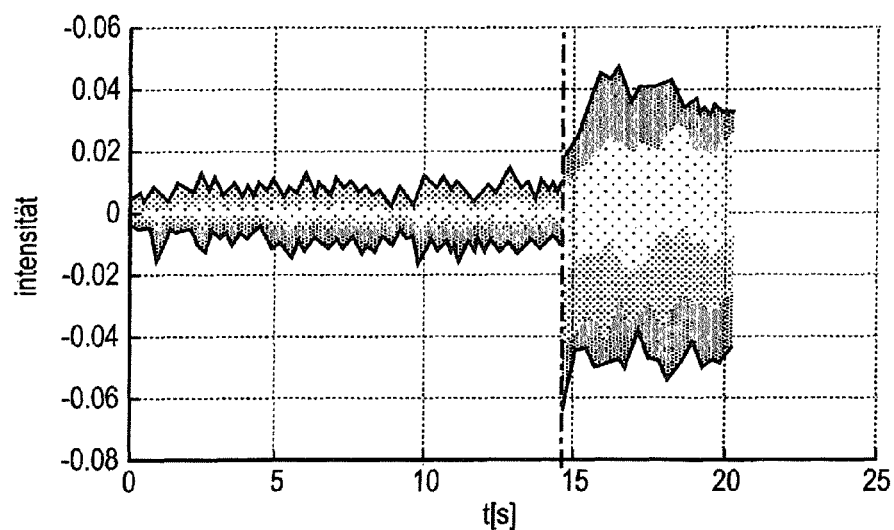
FIG. 5
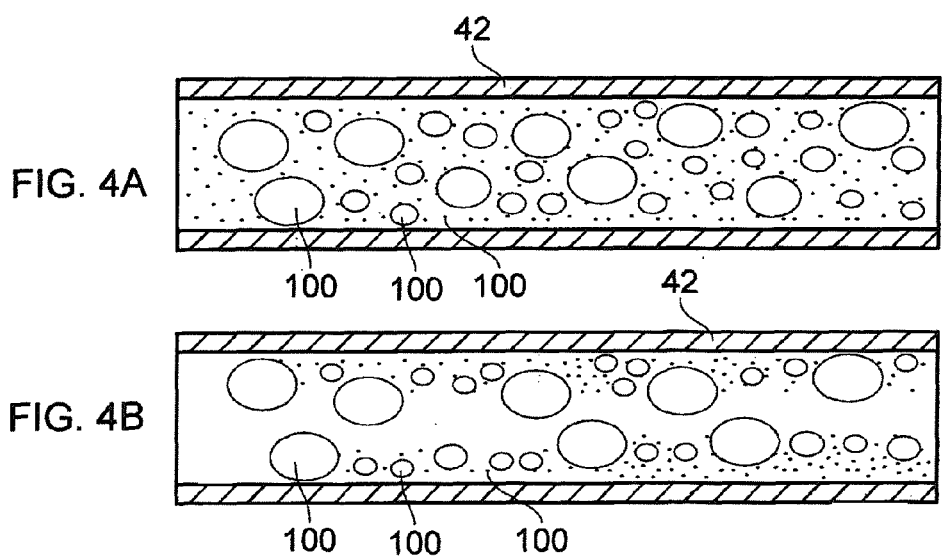
FIG. 4A
FIG. 4B

REACTION CARRIER, MEASURING SYSTEM AND MEASURING METHOD FOR DETERMINING GAS AND PARTICLE CONCENTRATIONS, AND OPTICAL FLOW SENSOR

CROSS REFERENCE TO RELATED APPLICATIONS

This application is a United States National Phase Application of International Application PCT/EP2014/001351 filed May 20, 2014 and claims the benefit of priority under 35 U.S.C. §119 of German Patent Application 10 2013 009 642.1 filed Jun. 8, 2013 the entire contents of which are incorporated herein by reference.

FIELD OF THE INVENTION

The present invention pertains to a measuring system for measuring a concentration of gaseous and/or aerosol components of a gas mixture and to a reaction carrier for such a measuring system with at least one flow channel, wherein the flow channel forms a reaction chamber with a reactant, which is designed to react with at least one component to be measured in the gas mixture or with a reaction product of the component to be measured in an optically detectable manner. The present invention pertains, furthermore, to a measuring method for measuring a concentration of gaseous and/or aerosol components of a gas mixture and to an optical flow sensor.

BACKGROUND OF THE INVENTION

Gas detector tubes, which are filled with a reactant, which reacts with a certain chemical compound in an optically detectable reaction, are known from the state of the art. For example, a defined quantity of a gas mixture is pumped through the gas detector tube, for example, with a hand pump. A concentration of the chemical compound to be measured is subsequently determined by means of a discoloration of the gas detector tube.

In addition, so-called chip-based measuring systems are known, in which the reactant is provided in a plurality of reaction chambers, which are arranged on a reaction carrier and which can be used for a measurement. The reaction carrier can be inserted into a measuring device, which detects the reaction carrier and carries out a corresponding measuring method for measuring a concentration of the corresponding component of the gas mixture. In case of measurements in which no concentration is measured, because the component to be measured is not present in the gas mixture or is present below a detection limit, a function test of the measuring system is necessary to rule out a malfunction.

SUMMARY OF THE INVENTION

An object of the present invention is to provide a simple sensor system for such a measuring system and a corresponding measuring method.

The object of the present invention is accomplished by a reaction carrier for a measuring system for measuring a concentration of gaseous and/or aerosol components of a gas mixture, with at least one flow channel, wherein the flow channel forms a reaction chamber with a reactant, which is designed to react with at least one component to be measured in the gas mixture or with a reaction product of the component to be measured in an optically detectable manner. The flow channel is filled at least partially with particles, which have a starting position before the gas mixture flows through the flow channel, and they are brought into a flow position by an admitted gas flow through the flow channel, wherein the particles are designed (configured) such that the particles in the starting position and the particles in the flow position can be optically distinguished. A flow of the gas mixture through the flow channel can be determined optically in this way, as a result of which the sensor system of a measuring device belonging to the measuring system can be simplified by, for example, the optically detectable reaction and the flow of the gas mixture being detected and determined via a common optical sensor. No separate sensor is thus needed for the determination of a mass flow.

It is possible that the particles have different sizes, and particles of different sizes are mixed in the starting position and the particles of different sizes are at least partially segregated in the flow position. Small particles are washed out by the gas flow and are deposited in areas with weak flow, and larger particles are oriented in the flow. The intensity distribution of the image of the flow channel changes due to this segregation, and the contrast is enhanced.

The particles may also have a flow shape in order to become oriented in their flow position in the direction of flow in a predetermined orientation in a gas flow. The particles can thus be oriented in a certain direction, and, in a particular, an isotropic or chaotic starting position can be distinguished from an oriented or ordered flow position. For example, the particles are drop-shaped.

It is also possible that the particles are marked in color in order to facilitate and enhance an optical distinction of the positions of the particles.

Furthermore, the particles may have mechanical, electric and/or magnetic properties in order to be moved back into a restored position by a mechanical, electric and/or magnetic restoring force acting on the particles, the particles being designed (configured) such that the particle in the restored position and the particles in the flow position can be optically distinguished. On the one hand, a measurement can be repeated or a continuous measurement can be performed in this way, because they are brought into their restored position by the restoring force acting on them and are thus moved into their restored position when the gas flow decreases. On the other hand, a first ordered distribution of the particles in their restored positions can be set compared to a second ordered distribution of the particles in their flow positions, as a result of which the determination of the positions of the particles can be simplified.

The present invention pertains, furthermore, to a measuring system for measuring a concentration of gaseous and/or aerosol components of a gas mixture with a reaction carrier according to one of the above claims and with a measuring device, which has an optical sensor, which detects the flow channel of the reaction carrier and is designed to optically determine the starting position and the flow position of the particles. A flow of the gas mixture through the flow channel can be determined optically in this way, as a result of which the sensor system of a measuring device belonging to the measuring system can be simplified, by, for example, the optically detectable reaction and the flow of the gas mixture being detected and determined via a common optical sensor. No separate sensor is thus needed for determining a mass flow.

Furthermore, the measuring device and/or the reaction carrier may be designed to generate an electric or magnetic field in the flow channel of the reaction carrier. An electric or magnetic restoring force can be generated in this way for corresponding particles.

The restoring force may be preferably modulated dynamically. The accuracy of the measurement can be improved in this way.

The present invention pertains, furthermore, to a measuring method for measuring a concentration of gaseous and/or aerosol components of a gas mixture with an above-described reaction carrier or with an above-described measuring system, with the method steps of recording a reference image of the flow channel before a delivery of a gas flow through the flow channel, wherein the particles are in a starting position; of recording a flow image of the flow channel during a delivery of a gas flow through the flow channel; and of determining the gas flow flowing through the flow channel by analyzing the reference image and the flow image. By analyzing the reference image and the flow image, a change in the position of the particles and thus a gas flow through the flow channel can be determined, as a result of which an optical determination of a gas flow through the flow channel is made possible.

According to a variant of the method, the measuring method comprises the method step of generating a restoring force during the delivery of the gas flow through the flow channel, which force brings the particles into a restored positioned. This makes possible a repeated or continuous measurement.

Furthermore, the measuring method may comprise the method step of a dynamic modulation of the restoring force during the delivery of the gas flow through the flow channel, so that the particles move to and fro between a restored position and a flow position. A continuous measurement can be carried out in this way with increased accuracy.

The present invention pertains, furthermore, to an optical flow sensor for determining a flow of a fluid, with a transparent flow channel, which is filled at least partially with particles. The particles have a flow shape in order to be oriented into a flow position in a gas flow in a predetermined orientation in the direction of flow and mechanical, electric and/or magnetic properties in order to be brought into a restored position by a mechanical, electric and/or magnetic restoring force acting on the particles, and the particles are designed (configured) such that the particles in the restored position and the particles in the flow position can be optically distinguished. Furthermore, a restoring device for generating the mechanical, electric and/or magnetic restoring force, an optical sensor element, which is designed (configured) to detect a change in the position of the particles from the starting position into the flow position, and a control unit, which is designed (configured) to determine the flow of the fluid by means of the detected change in the position of the particles, are provided. Such a flow sensor makes possible an optical determination of a flow through the flow channel.

The above-described embodiments may be combined with one another and with the above-described aspects as desired in order to achieve advantages according to the present invention. Further features and advantages of the present invention appear from the embodiments described below The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 4a is a schematic sectional view of a flow channel according to a first embodiment of a reaction carrier with particles in their starting position;

FIG. 4b is a schematic sectional view of a flow channel according to the first embodiment of a reaction carrier with particles in their flow position;

FIG. 5 is a diagram of an intensity distribution of images of the flow channel according to the first embodiment;

DESCRIPTION OF THE PREFERRED EMBODIMENTS

Figure 1:
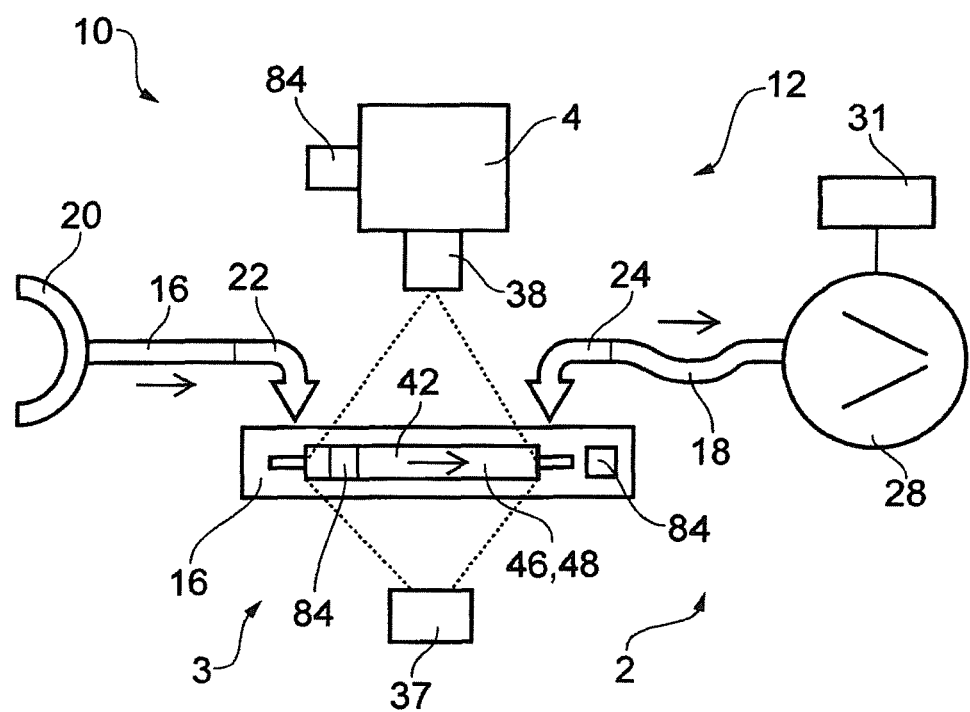
FIG. 1 is a schematic view of a first embodiment of a measuring system according to the present invention with a measuring device and with a reaction carrier according to the present invention.

Referring to the drawings, FIG. 1 shows a schematic view of a gas-measuring system, hereinafter also called measuring system 10. The measuring system 10 comprises a measuring device 12 and a reaction carrier 14. The reaction carrier 14 has at least one flow channel 42, which forms a reaction chamber 46 with a reactant 48. The reactant 48 is designed to react with at least one component to be measured in a gas mixture or with a reaction product of the component to be measured in an optically detectable manner. The component to be measured can either react in this way directly with the reactant or an intermediate reaction may be provided, in which the component to be measured reacts with an intermediate reactant and the reaction product formed in the process subsequently reacts with the reactant in an optically detectable manner.

The measuring device 12 comprises a gas delivery unit 2 with a gas delivery device 28 for delivering the gas mixture through the flow channel 42 of the reaction carrier 14.

The gas delivery unit 2 comprises, furthermore, a gas inlet channel 16 with a gas mixture inflow opening 20, through which the gas mixture can flow into the gas inlet channel 16, and a gas port 22, which may be connected to the flow channel 42 of the reaction carrier 14.

Furthermore, the gas delivery unit 2 comprises a gas outlet channel 18 with a gas port 24, which may be connected to the flow channel 42 of the reaction carrier 14. The gas delivery device 28 is arranged in the gas outlet channel 18 and makes it possible to deliver the gas mixture in a direction of flow indicated by arrows in FIG. 1.

A control/regulation unit 31 is provided, which is designed (configured) to control or regulate a flow of the gas mixture through the flow channel as a function of at least one reaction rate parameter. Reaction rate parameters may be, for example, the speed of propagation of a reaction front of the optically detectable reaction or a temperature of the gas mixture flowing through the flow channel 42. Temperature-measuring elements 84, make possible a measurement of the temperature of the gas mixture directly in the flow channel 42 of the reaction carrier 14, or indirectly via a measurement of the temperature of the reaction carrier 14 and/or of the measuring device 12.

The measuring device 12 comprises, moreover, a detection unit 3 with a lighting device 37 for illuminating the reaction chamber 46 of the reaction carrier 14. In the embodiment being shown, the lighting device 37 is designed to illuminate the reaction chamber with a broad-band spectrum. The broad-band spectrum corresponds, for example, to white light. However, other adjacent spectral ranges, as well as infrared spectral ranges or ultraviolet spectral ranges may also be covered by the broad-band spectrum.

The detection unit 3 comprises, furthermore, an optical sensor 38 for detecting the optically detectable reaction in the reaction chamber 36 of the reaction carrier 14, as well as an analysis unit 4 for analyzing the data of the optically detectable reaction, which were detected by the optical sensor, and for determining a concentration of the component of the gas mixture.

The optical sensor 38 is a multichannel sensor, which can detect a plurality of color channels. The optical sensor 38 is designed in the embodiment being shown as a digital camera, and will hereinafter also be called digital camera 38.

The analysis unit 4 is designed (configured) to perform a weighting of the color channels during the analysis of the data of the optical sensor 38.

For the sake of clarity, the lighting device 37 is arranged in FIG. 1 on the side of the reaction carrier 14 located opposite the optical sensor 38. However, the lighting device may also be arranged in different positions on the measuring device 12 and make a corresponding illumination possible. For example, the illumination and the observation by the optical sensor 38 may take place from the same direction and thus on the same side of the reaction carrier 14.

The detection unit 3 comprises, furthermore, an analysis unit 4, which is designed (configured) to determine the concentration of the component to be measured in the gas mixture exclusively from optically determinable parameters of the reaction front. For this, in case of a detection of a reaction front propagating in the reaction chamber 46, the front speed and an intensity gradient of the reaction front propagating in the direction of flow in the reaction chamber 46 are, for example, measured and the concentration of the component to be measured is determined therefrom.

However, in case the gas mixture does not contain the component to be measured or does contain this below a detection threshold, a function test of the measuring system 10 must be performed in order to rule out an error of measurement based on a malfunction of the measuring system, for example, on the basis of a leakage or clogging of the flow channel.

Figure 2:
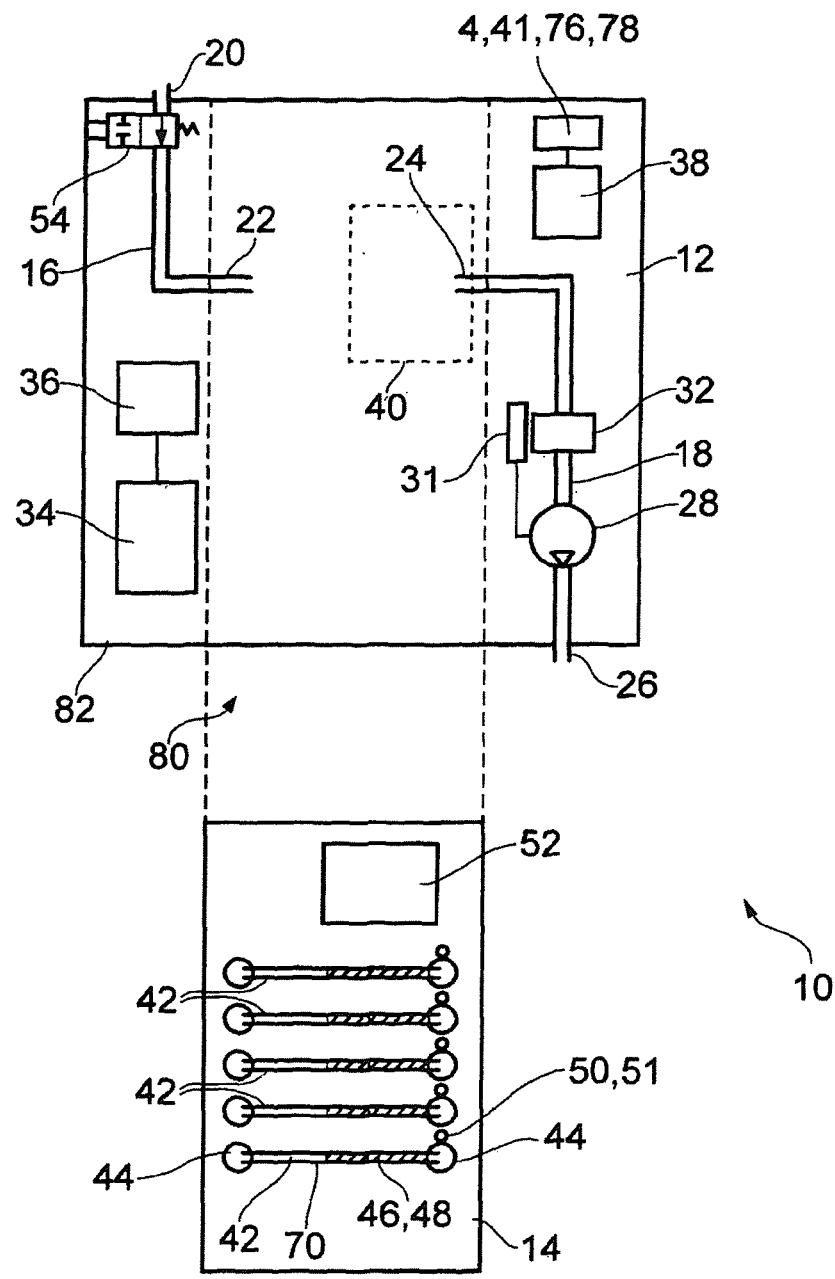
FIG. 2 is a detailed view of the measuring system from FIG. 1.
Figure 3:
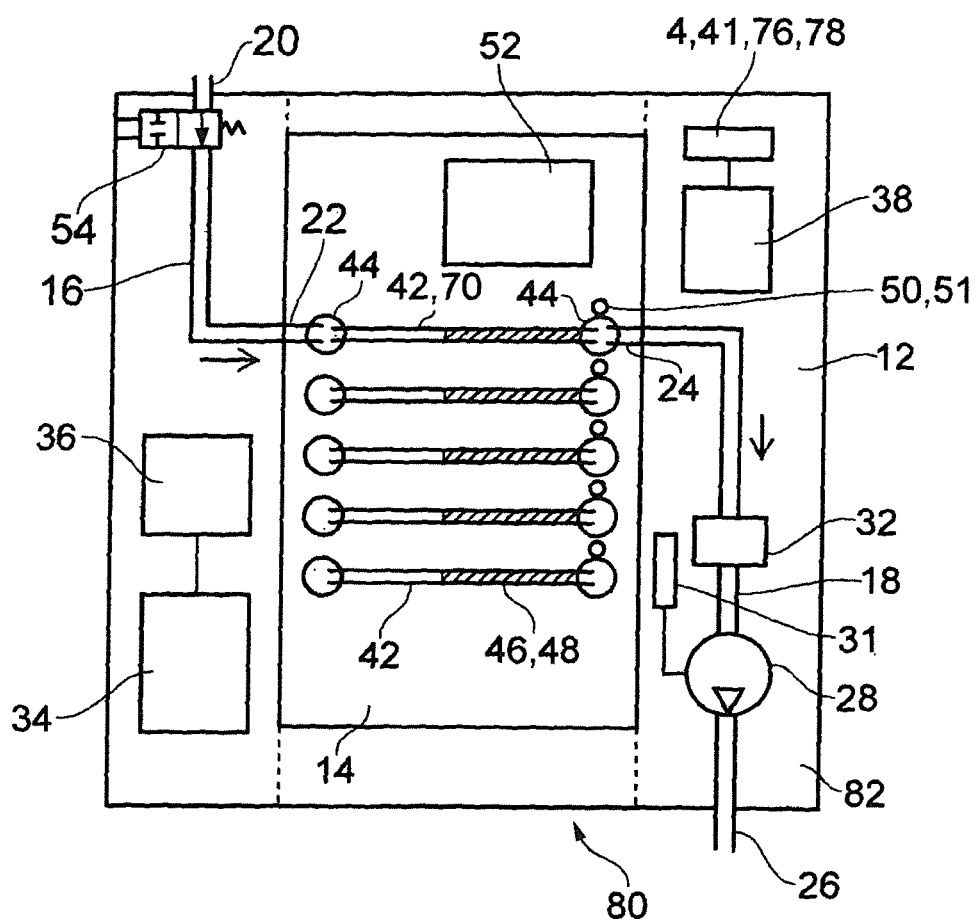
FIG. 3 is a detailed view of the measuring system from FIG. 1 with the reaction carrier inserted.

FIGS. 2 and 3 show a more detailed view of the measuring system 10 for measuring and detecting the concentration of gaseous and/or aerosol components. A replaceable reaction carrier 14, also called reaction carrier unit, is inserted manually by a user into the measuring device 12, also called gas-measuring device or otherwise gas-measuring system. The measuring system 10 or the measuring device 12 is a small, portable device, which can be used under mobile conditions and is provided with a battery as an energy supply. FIG. 2 shows the measuring device 12 and the reaction carrier 14 separately and FIG. 3 shows the measuring device 12 with the reaction carrier 14 inserted into it.

The gas delivery device 28, which is embodied by a pump designed as a suction pump, is arranged on a housing of the measuring device 12. In addition, the housing forms a mount, especially a sliding mount, for the displaceable reaction carrier 14. The reaction carrier can be moved within the housing of the measuring device by means of a reaction carrier delivery device 34 with a motor, e.g., with an electric motor designed as a servomotor and a rotatable gear mechanism, especially driving roller, because there is a mechanical contact or a connection between the driving roller and the reaction carrier.

The measuring system 10 comprises the measuring device 12 and at least one reaction carrier 14. The gas flow channel 16 extends from the gas mixture inflow opening 20 to the first gas port 22. The gas outlet channel 18 extends from the second gas port 24 to a gas mixture outflow opening 26.

The gas inlet channel 16 is made of glass, as a result of which a chemical reaction or a deposit of gas components on the wall of the gas inlet channel is prevented or reduced.

A valve 54 is arranged at the gas mixture inflow opening 20 upstream of the gas inlet channel 16. The valve makes possible a gas flow through the gas inlet channel 16 in its first position shown, and prevents a gas flow through the gas inlet channel 16 in a second position. The valve 54 is designed as a 2/2-way valve in the embodiment being shown.

However, it is also possible that the measuring device 12 is made without a valve 54 at the gas mixture inflow opening 20. The number of components through which the gas mixture flows before the reaction chamber 46 can be reduced in this way and a chemical reaction or deposit of gas components on the components can thus be prevented or reduced.

Furthermore, a buffer 32, which makes a uniform gas flow through the gas outlet channel 18 possible, is arranged in the gas outlet channel 18.

The measuring device 12 comprises, moreover, a reaction carrier delivery device 34, which makes it possible to move the reaction carrier 14 relative to the gas inlet channel 16 and the gas outlet channel 18.

A position sensor 36 is used to detect a relative position of the reaction carrier 14 and of the gas ports 22, 24.

The optical sensor 38 for detecting an optically detectable reaction is provided in the form of a digital camera 38 and it makes it possible to record the recording field 40 indicated by the dotted rectangle in FIG. 1.

A central control unit 41 is provided, which can process the data detected by the optical sensor and controls the measuring method. The central control unit comprises the analysis unit 4 in the embodiment being shown.

The reaction carrier 14 has a plurality of flow channels 42, which extend each between two connection elements 44. In the embodiment being shown, each of the flow channels 42 forms a reaction chamber 46, which is filled with reactant 48. The reactant 48 is a chemical compound, which reacts with a gas and/or an aerosol component to be measured in a gas mixture in an optically detectable manner. This is, for example, colorimetric reaction.

In the embodiment being shown, the flow channels 42 are each filled with the reactant 48 on their right side. Another gas treatment element, for example, a desiccant, is provided on the left side of the flow channels 42.

A display pin 50, which forms a code 51, which is detected by the position sensor 36 and makes it possible to position the reaction carrier 14 independently in relative positions each associated with the flow channels 42, is associated with each flow channel 42. Another type of code 51, for example, an electric, electronic or magnetic code, which can be detected by a corresponding position sensor 36, may also be provided. However, an optical code 51 is provided, at least additionally, in order for a user of the measuring system 10 to be able to determine, by looking at the reaction carrier 14, at a first glance whether the reaction carrier still has unused reaction chambers.

The reaction carrier 14 has, furthermore, an information field 52, on which information is stored. In the embodiment being shown, the information field 52 is designed as an optical information field, on which information that can be read by the digital camera 38 is stored. As an alternative, the information field 52 may be provided as an electronic memory for information and designed (configured), for example, as an RFID chip or SROM chip, which can be read and/or written on in a wireless manner or via electric contacts.

The recording field of the digital camera 38 is designed in the embodiment being shown such that the reaction chambers 46, the display pins 50, and the information field 52 are each detected by the digital camera 38 at least in a relative position of the reaction carrier 14 in the measuring device 12. The digital camera 38 may be used in this way, on the one hand, for detecting the optically detectable reaction of the reactant 48 in the reaction chambers 46 of the reaction carrier 14 and, on the other hand, for reading the information in the information field 52 and as a position sensor 36 for detecting the relative position of the reaction carrier and the gas ports 22, 24. However, it is also possible that the position sensor 36 and a reading device for reading the information field 52 are designed as one or two separate devices.

A function test of the measuring system 10, especially for the case in which the gas mixture does not contain the component to be measured or this is present below a detection threshold, at which a flow through the flow channel can be measured via the optical sensor 38, will be described below.

FIGS. 4A and 4B show each an enlarged section of a flow channel 42 of a reaction carrier 14 according to a first embodiment. The flow channel 42 is filled with particles 100. According to the first embodiment, the particles 100 have different sizes, and the particles 100 of different sizes are present in a mixed state in the starting position of the particles 100 shown in FIG. 4A. FIG. 4A shows the detail of the flow channel 42 at a time before a gas mixture flows through the flow channel 42, at which time the particles 100 are each in a starting position.

FIG. 4B shows the detail of the flow channel 42 at a time at which a gas mixture is flowing through the flow channel 42. The particles 100 are brought by the admitted gas flow into a flow position. In the first embodiment shown in FIG. 4B, the particles 100 of different sizes are segregated at least partially by the gas flow. For example, fine particles are washed out and they are deposited at sites with lower flow velocity. Large particles can change their orientation in the gas flow and perform, for example, a rotary motion. The particles are designed (configured) such that the particles 100 in the starting position shown in FIG. 4A and the particles 100 in the flow position shown in FIG. 4B can be optically distinguished. The above-described changes in the positions of the particles of different sizes lead to a changed intensity distribution in images of the flow channel 42 recorded before the gas flow and during the gas flow.

FIG. 5 shows a diagram of the intensity profiles of all image pixels of an image of a flow channel according to the first embodiment, the vertical axis showing a deviation from a mean value, and with the time being plotted on the horizontal axis, wherein the time at which the gas mixture flows through the flow channel, i.e., the start of the gas delivery device 28, is indicated by the vertical broken line. Before the delivery of a gas flow through the flow channel, in the left-hand half of the diagram, the intensity profiles show a smaller deviation from the mean value. As soon as the gas flow flows through the flow channel 42, the particles 100 are brought by the flow into their flow position, and the particles 100 of different sizes become at least partially segregated. The change in the positions of the particles 100 brings about a change in the image, and the segregation of the particles 100 of different sizes brings about a contrast enhancement and is detectable from a markedly increased deviation from the mean value in the intensity distribution. It is thus possible to check based on the optically detectable change in the positions of the particles 100 whether a mass flow has taken place through the flow channel. The function of the gas delivery unit 2 can be checked in this way.

The size distribution of the particles 100 of different sizes is selected to be such that the greatest possible change in the deviation of the intensity distribution is obtained in case of a change in the positions of the particles 100. The particles 100 may be formed by the reactant 48 or may consist of another substance and mixed with the reactant 48 or arranged in a separate section of the flow channel 42. The particles 100 of different sizes preferably comprise very fine-grained particles, which are washed out immediately during a gas flow and lead to a rapid change in the positions of the particles 100 and to a rapid detection of the gas flow.

Figure 6:
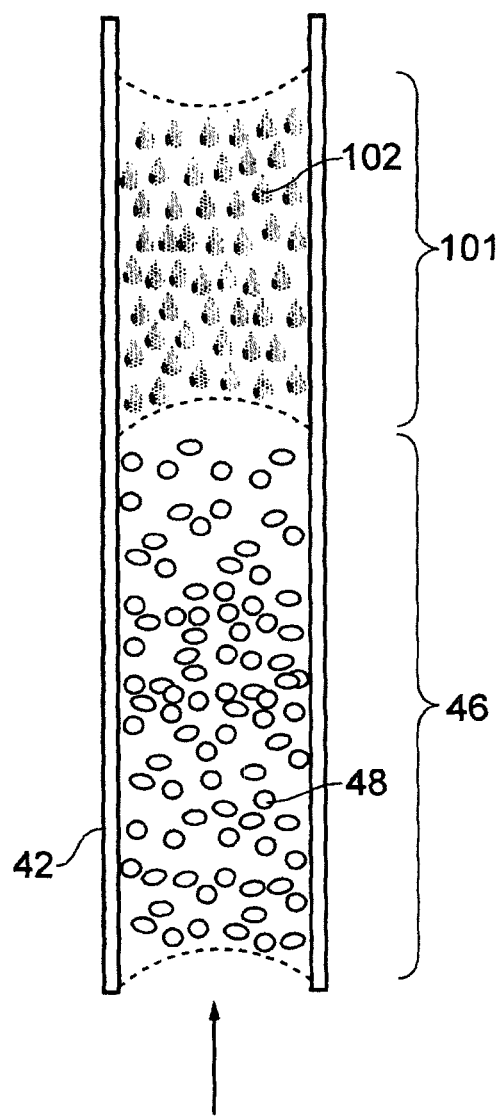
FIG. 6 is a schematic sectional view of a flow channel according to a second embodiment of a reaction carrier.

FIG. 6 shows a detail of a flow channel 42 with a second embodiment of a reaction carrier 14. The flow channel 42 comprises a first section on the left side, which forms the reaction chamber 46 with the reactant 48, and a second section 101 on the right side, which is filled with particles 102, the particles having a flow shape. The flow shape of the particles 102 causes the particles to be oriented into a defined flow position in a predetermined orientation in the direction of flow in a gas flow. A gas flow takes place in FIG. 6 from left to right, as is indicated by the arrow, and all particles 102 are oriented in their flow position.

Figure 7A:
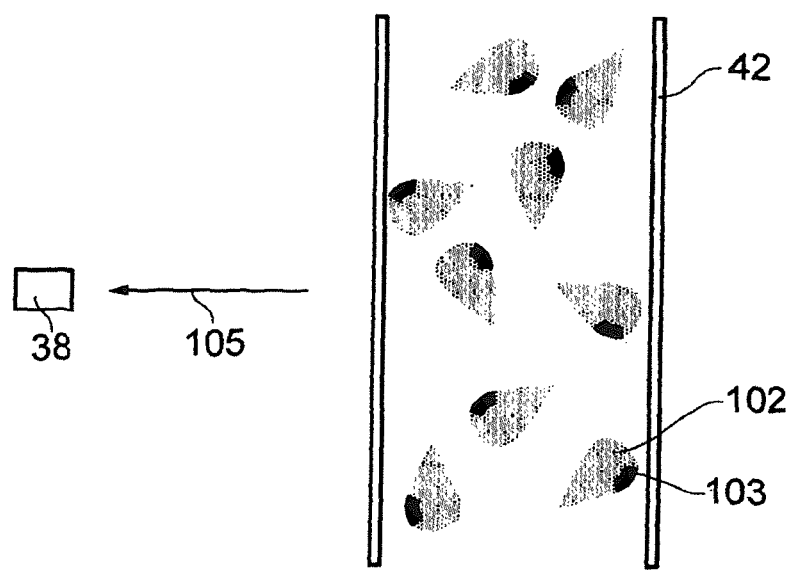
FIG. 7a is a sectional view of the flow channel according to FIG. 6 with particles in their starting position.
Figure 7B:
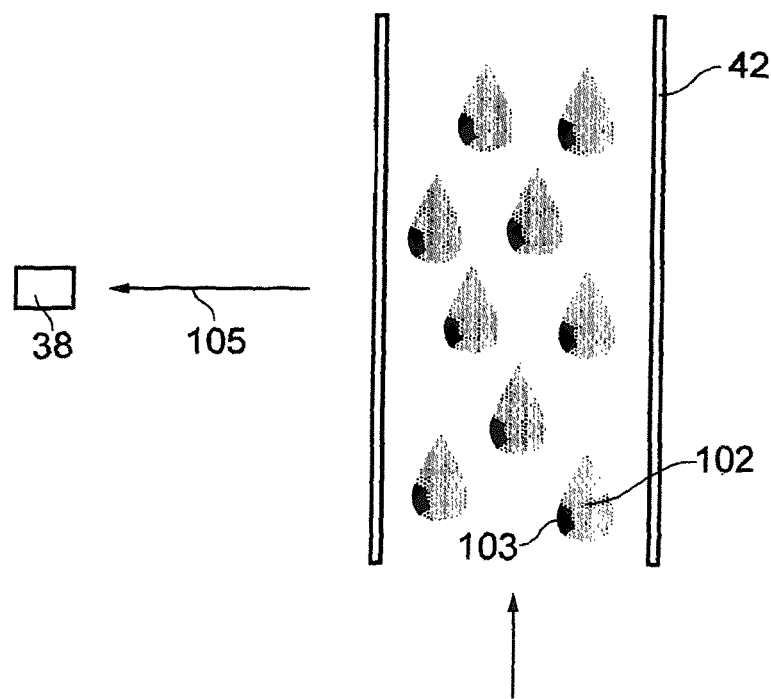
FIG. 7b is a schematic sectional view of the flow channel according to FIG. 6 with particles in their flow position.

FIGS. 7A and 7B show a detail view each of the second section 101 of the second embodiment. In the embodiment being shown, the particles 102 having a flow shape are drop-shaped and have a color marking 103. However, it is also possible to select another flow shape, which brings about an orientation of the particles 102 in a predetermined orientation in the direction of flow, for example, a rod shape or a disk shape.

The color marking 103 may be provided, on the one hand, for a better distinction of the particles from other particles in the flow channel 42, for example, reactant 48. On the other hand, the color marking may be designed such that the color marking is oriented in the flow position such that a better optical distinction is made possible between the starting position and the flow position of the particles 102 having a flow shape.

FIG. 7A shows a detail view of the second section 101 of the second embodiment, in which the particles 102 having a flow shape are arranged in a starting position. The orientation of the particles is essentially random in the starting position.

FIG. 7B shows the detail view of the second section 101 with a flow through the flow channel 42 in the direction of the arrow. The particles 102 are brought by the flow into their flow position and rotate in their predetermined orientation in the direction of flow. Homogeneous distribution of the color markings 103 is obtained in the embodiment being shown compared to the distribution shown in FIG. 7A due to the regular arrangement of the particles 102 in their flow position compared to the chaotic random orientation of the particles 102 in the starting position.

The color marking 103 or the particle shape is selected to be such that the color markings 103 or an area of the particles 102 in relation to a certain observation direction 105 of the optical sensor 38 in the flow position is oriented towards the observation direction, while the color markings 103 or the surfaces of the particles are visible only partially in the observation direction in the starting position.

Figure 8A:
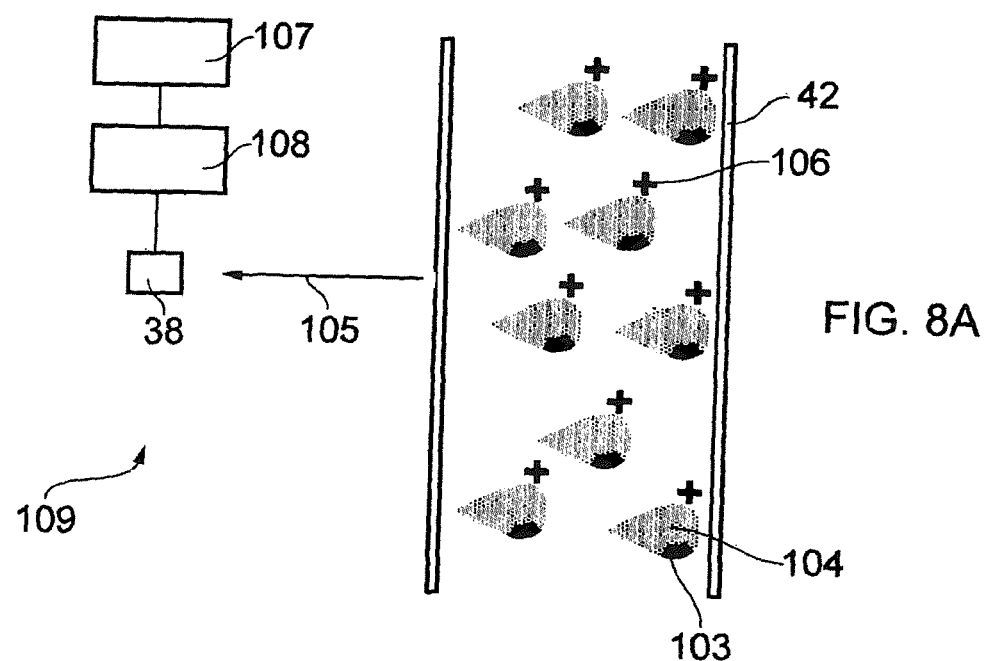
FIG. 8a is a sectional view of the flow channel of a reaction carrier according to a third embodiment with particles in their restored position.
Figure 8B:
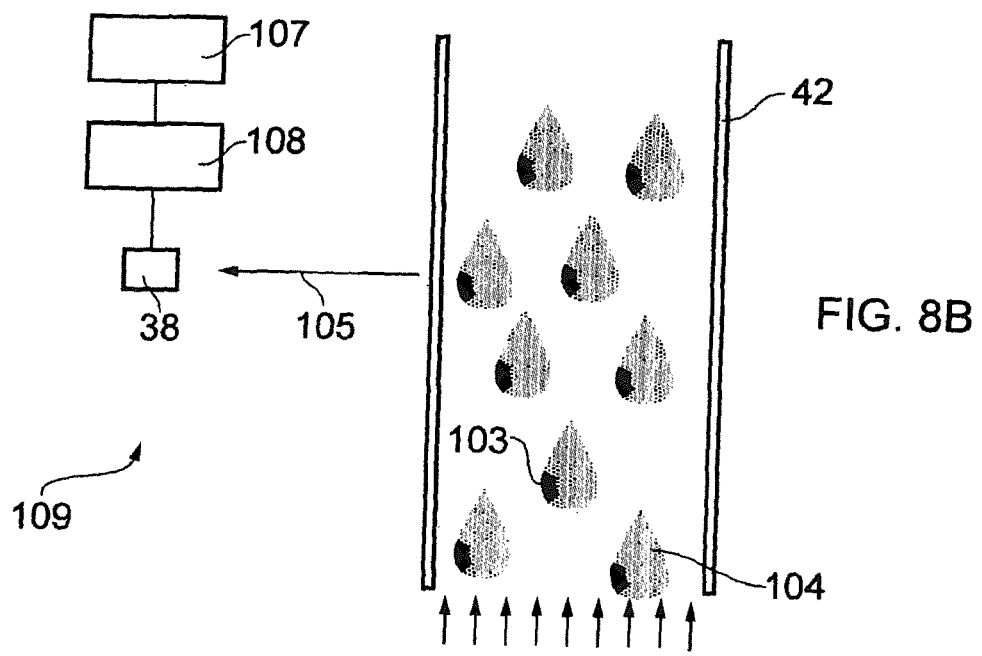
FIG. 8b is a sectional view of the flow channel of a reaction carrier according to the third embodiment with particles in their flow position.

FIGS. 8A and 8B show a flow channel 42 of a reaction carrier 14 according to a third embodiment. The flow channel 42 is filled at least partially with particles 104, which have a flow shape analogously to the preceding embodiment. In addition, the particles 104 of the third embodiment possess an electric property in order to be moved into a restored position by an electric restoring force acting on the particles 104, the particles 104 being designed (configured) such that the particles in the restored position and the particles 104 in the flow position can be optically distinguished.

The electric property is an electric dipole moment in this embodiment, and the particles 104 may have a permanent dipole moment or an induced dipole moment. The electric restoring force is generated by an external electric field, in which the electric dipoles are oriented. In the embodiment being shown, the electric field is represented by the field lines 106 in FIG. 8A. The electric field is generated by a restoring device 107. The restoring device 107 may be formed in the measuring device 12 or in the reaction carrier 14, for example, by capacitor plates extending in parallel to the flow channel 42.

An optical flow sensor 109 is formed by the transparent flow channel 42 with the particles 104, the restoring device 107, the optical sensor element 38 for detecting the change in the positions of the particles and a control unit 108, which is designed (configured) to determine the flow of a gas or of another fluid by means of the detected change in the positions of the particles 104. The flow sensor 109 may also be used to measure the flow of other fluids, besides the use shown in an above-described measuring system 10.

FIG. 8A shows the particles 104 in their restored position, in which the particles 104 are oriented in the electric field 106. It is also possible in this embodiment to move the particles by the restoring force, at the beginning of a measurement, into their restored position, in which the particles 104 have a defined orientation. The optical contrast can be improved in this way at the time of a change in the positions of the particles 104 by, for example, color markings 103 or certain surfaces of the particles 104 pointing towards the observation direction 105 in one position and pointing away from the observation position 105 in the other position.

Due to the particles 104 being able to be brought into a defined restored position by the restoring force, it is also possible to perform repeated or continuous measurements. Thus, the particles 104 can be oriented into their restored position at the beginning of each measurement by applying an electric field, and the particles 104 are oriented in their flow position if a flow is present after the electric field has been switched off.

In addition, a sensitivity of the measurement can be set by a weak restoring force bringing the particles 104 into their restored position and a sufficient force acting on the particles 104 in the direction of the flow position only in case of a certain intensity of flow, so that a change in position occurs towards the flow position.

Further, a dynamic modulation of the restoring force may be performed by the restoring device 107. The dynamic modulation may be performed, for example, such that the particles 104 move to and fro between the restored position and the flow position, for example, with sinusoidal voltage with settable offset, or they are held at a changeover point by means of a control circuit, the measurement becoming in this way largely independent from the mechanical properties of the particles. The voltage necessary for this is then used as an indicator of the flow velocity.

Figure 9:
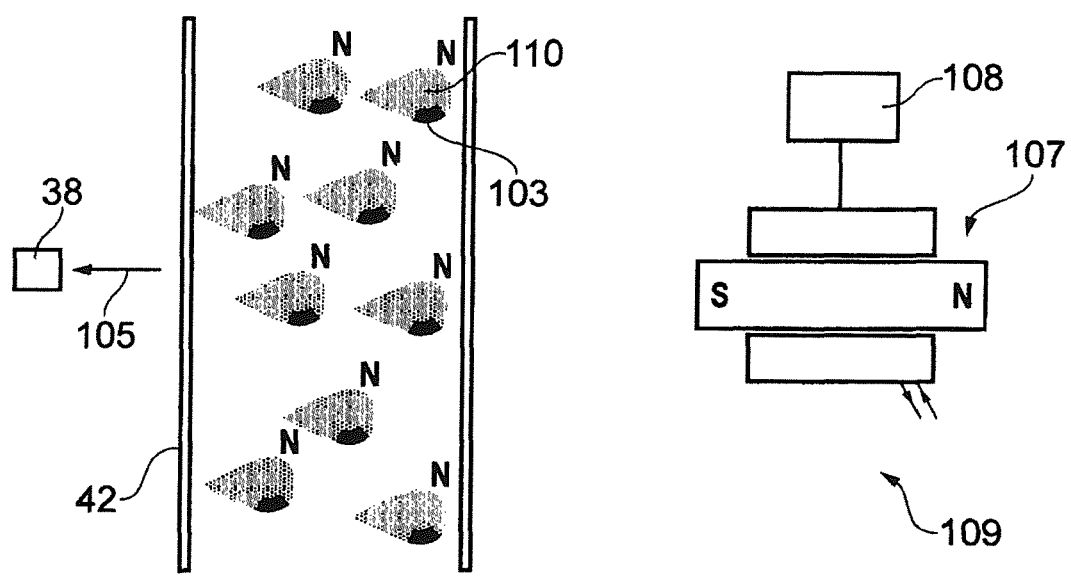
FIG. 9 is a sectional view of the flow channel of a reaction carrier according to a fourth embodiment with particles in their restored position.

FIG. 9 shows an alternative embodiment of an optical flow sensor 109 with a flow channel 42 according to a fourth embodiment of a reaction carrier 14. The particles 110 have, analogously to the second and third embodiments, a flow shape and additionally possess magnetic properties in order to be moved into a restored position by a magnetic restring force acting on the particles, said particles 110 being designed (configured) such that the particles 110 in the restored position and the particles in the flow position can be optically distinguished.

A restoring device 107 generates a magnetic field, in which the particles 110 are oriented into their restored position, as is shown in FIG. 9. The measurement is carried out essentially analogously to the above explanations, but the magnetic field is changed instead of the electric field. The particles 110 are, for example, metallic particles.

It is also possible that particles 100, 102, 104 or 110 are provided, which possess mechanical properties in order to be moved into a restored position by a mechanical restoring force acting on the particles, said particles being designed (configured) such that the particles in the restored position and the particles in the flow position can be optically distinguished. For example, the particles may be embedded in an elastic matrix or form an elastic matrix themselves. The particles may also possess electric properties, for example, due to magnetization or a permanent electric dipole moment, so that the particles interact with one another and a preferred position of the particles, which represents a restored position, develops.

It is also possible, in particular, to combine the above-mentioned different embodiments with one another. For example, the particles 104 having an electric dipole moment may thus be embedded in an elastic matrix, and an adjustable electric restoring force, on the one hand, and an invariable mechanical restoring force, on the other hand, may thus act on the particles 104.

On the one hand, a determination on the basis of a fixed or variable threshold value may be provided as an indicator for the flow, in which case it is determined that a flow above the threshold value is present. On the other hand, the contrast due to the change in position may be used as an indicator for the intensity of flow, or a variable restoring force may be used, for example, via the restoring force needed for the restoring to determine the intensity of flow.

A measuring method will be described below with reference to FIGS. 2 and 3.

The reaction carrier 14 is inserted into an insertion opening 80 in a housing 82 of the measuring device 12. The reaction carrier 14 is inserted manually into the insertion opening, detected by the reaction carrier delivery device 34 and transported forward in the insertion direction.

The information field 52 of the reaction carrier 14 passes through the recording field 40 of the digital camera 38 during the transportation of the reaction carrier 14, and the information on the information field 52 is detected by the digital camera 38 and can be analyzed in an analysis unit of the central control unit 41. It is also possible that the reaction carrier is positioned in a reading position, in which reading of the information field 52 is made possible. The information is stored optically on the information field 52 in the embodiment being shown and can thus be read by the digital camera 38 in a simple manner. It is also possible, as an alternative, that an electronic information field 52 is provided, which is designed, for example, as an active or passive RFID chip or SRAM chip and can be read in a wireless manner or via electric contacts. The electric contacts are preferably established via data lines to the inflow and outflow openings of the flow channels 42 and gas connection pieces made of a current-carrying material, so that a current and data connection is established between the SRAM chip and a corresponding reading device, while the gas connection pieces are located in the inflow and outflow openings.

The information of the reaction carrier 14, especially relating to the component to be measured in the gas mixture and a corresponding concentration range, which information is contained on the information field 52, is read in a first method step.

The reaction carrier 14 is subsequently positioned in a position relative to the gas ports 22, 24 of the measuring device 12, and a flow channel 42 is selected, which has an unused reaction chamber 46, the flow channel selected being the first flow channel 42 of the reaction carrier 145 in the insertion direction in the example shown in FIG. 3.

A connection is established between the gas ports 22, 24 by the second flow channel 42.

A reference image of the flow channel 42 is recorded before the start of the gas delivery device 28, the particles 100, 102, 104 or 110 being located in a starting position. If provisions are made, the particles 104 or 110 may also be brought into their restored positions by the restoring forces before the reference image of the flow channel 42 is recorded. The restored position corresponds to the starting position in this case.

After recording the reference image, the gas delivery device 28 delivers a gas mixture to be measured through the outlet channel 18, the second flow channel 42 and the gas inlet channel 16, and the digital camera 38 detects a possible optically detectable reaction in the reaction chamber 46.

The digital camera 38 records a flow image of the flow channel 42 during the delivery of the gas mixture by the gas delivery device 28. This flow image may be used for both the optical detection of the flow through the flow channel 42 and for the detection of the optically detectable reaction.

The control unit 108 analyzes the reference image and the flow image of the digital camera 38 and determines the flow of the gas flow flowing through the flow channel 42 by means of the detected change in the positions of the particles 100, 102, 104, 110.

The digital camera 38 preferably records flow images of the flow channel 42 continuously in order to make possible a continuous optical detection of the flow through the flow channel 42 and of the optically detectable reaction.

The measuring system 10 preferably generates a restoring force during the delivery of the gas flow, which restoring force brings the particles into a restored position. The accuracy of the determination of the intensity of flow can be increased by adaptation and especially dynamic modulation of the restoring force.

The detection unit 3 detects a reaction front propagating in the direction of flow in the reaction chamber 46 and the speed thereof during the delivery of the gas mixture and determines a preliminary measurement result of the concentration of the component to be measured in the gas mixture from the speed of the reaction front.

A final measurement result of the concentration of the component of the gas mixture is determined and outputted after the end of delivery of the gas mixture.

If the component to be determined in the gas mixture is not contained in the gas mixture or is present at a concentration below a detection threshold of the concentration range of reaction carrier 14, no optically detectable reaction is detected in the reaction chamber 46, and no reaction front will consequently develop in the reaction chamber 46.

A corresponding result of the measurement is displayed by the measuring device, for example, optically or acoustically.

A checking is preferably performed for leakage flows each time a connection is established between the gas ports 22, 24 via a flow channel 42.

In a first step, the gas port 24 of the gas outlet channel 18 is connected to the corresponding connection element 44 of the reaction carrier 14. Gas is delivered in a second step through the gas outlet channel 18 and the flow channel 42 of the reaction carrier 14, which said flow channel is connected thereto, and the gas flow through the gas outlet channel is measured to check for leakage flows. If the system comprising the gas outlet channel and the flow channel is gas-tight, no gas flow is essentially measured through the gas outlet channel 18, because the flow channel 42 of the reaction carrier 14 is closed in a gas-tight manner via the second connection element 44 closed by the sealing device 62.

In a further step, the gas inlet channel 16 is closed upstream by the valve 54 and the gas port 22 of the gas inlet channel 16 is connected to the corresponding connection element 44 of the reaction carrier 14. Gas is subsequently delivered through the gas outlet channel 18, the flow channel 42 and the gas inlet channel 16, and the gas flow through the gas outlet channel is measured for checking for leakage flows. If the system comprising the gas outlet channel 18, the flow channel 42 and the gas inlet channel 16 is gas-tight, no gas flow is essentially measured through the gas outlet channel 18, because the gas inlet channel 16 is closed in a gas-tight manner by the valve 54.

The measurement of an essentially zero gas flow during the measurement described in the preceding paragraphs in a gas-tight measuring system 10, in which normal pressure is present in the gas outlet channel 18, the flow channel 42 and/or the gas inlet channel 16 before the checking for leakage flows, should be interpreted such that an essentially exponentially decreasing gas flow following the vacuum is measured. In other words, the measured gas flow in a gas-tight measuring system 10 corresponds to the quantity of gas present in the channels 16, 18, 42 at the start of the measurement, which quantity is pumped off by the gas delivery device 28 at the time of the checking for leakage flows.

If a leakage flow, i.e., a gas flow exceeding the gas flow mentioned in the preceding paragraph is measured through the gas outlet channel 18, a corresponding error message is sent by the measuring device 12. The flow channel 42 on the reaction carrier 14 or gas outlet channel 18 and gas inlet channel 16 of the measuring device 12 can then be checked, for example, by the user.

It is also possible that both gas ports 22, 24 of the gas outlet channel 18 and of the gas inlet channel 16 are connected to the corresponding connection elements 44 of the flow channel 42 already in a first step, and a single checking for leakage flows is correspondingly performed.

While specific embodiments of the invention have been shown and described in detail to illustrate the application of the principles of the invention, it will be understood that the invention may be embodied otherwise without departing from such principles.

The invention claimed is:

1. A reaction carrier for a measuring system for measuring a concentration of gaseous and/or aerosol components of a gas mixture the reaction carrier comprising:
at least one flow channel, wherein the flow channel forms a reaction chamber with a reactant, which is configured to react with at least one of the components to be measured in the gas mixture or with a reaction product of the component to be measured in an optically detectable manner;
particles at least partially filling the flow channel the particles having a starting position before the gas mixture flows through the flow channel, and a flow position, wherein the particles are configured to move in the flow channel from the starting position to the flow position via the gas mixture flowing through the at least one flow channel, wherein the particles in the starting position are optically distinguishable from the particles in the flow position.

2. A reaction carrier in accordance with claim 1, wherein the particles have different sizes and wherein particles of different sizes are mixed in the starting position and the particles of different sizes are at least partially segregated in the flow position.

3. A reaction carrier in accordance with claim 1, wherein the particles have a flow shape in order to be oriented into their flow position in a gas flow in a predetermined orientation in the direction of flow.

4. A reaction carrier in accordance with claim 1, wherein the particles possess mechanical, electric and/or magnetic properties in order to be moved into a restored position by a mechanical, electric and/or magnetic force acting on the particles, the particles being configured such that the particles in the restored position and the particles in the flow position can be optically distinguished.

5. A reaction carrier in accordance with claim 2, wherein the particles have a flow shape in order to be oriented into their flow position in a gas flow in a predetermined orientation in the direction of flow.

6. A reaction carrier in accordance with claim 5, wherein the particles possess mechanical, electric and/or magnetic properties in order to be moved into a restored position by a mechanical, electric and/or magnetic force acting on the particles, the particles being configured such that the particles in the restored position and the particles in the flow position can be optically distinguished.

7. A reaction carrier in accordance with claim 2, wherein the particles possess mechanical, electric and/or magnetic properties in order to be moved into a restored position by a mechanical, electric and/or magnetic force acting on the particles, the particles being configured such that the particles in the restored position and the particles in the flow position can be optically distinguished.

8. A reaction carrier in accordance with claim 3, wherein the particles possess mechanical, electric and/or magnetic properties in order to be moved into a restored position by a mechanical, electric and/or magnetic force acting on the particles, the particles being configured such that the particles in the restored position and the particles in the flow position can be optically distinguished.

9. A reaction carrier in accordance with claim 1, wherein the reactant comprises a chemical compound, which reacts with the at least one of the components to be measured in the gas mixture or with the reaction product of the component to be measured upon the gas mixture being introduced into the at least one flow channel, the at least one of the components to be measured in the gas mixture being a gas component to be measured in the gas mixture, the reaction product of the component to be measured being an aerosol component.

10. A reaction carrier in accordance with claim 1, wherein the at least one channel comprises an inlet, an outlet, a closed state and an open state, the inlet and the outlet being sealed in the closed state, wherein the gas mixture passes through the inlet and the outlet in the open state.

11. A reaction carrier in accordance with claim 1, wherein the reaction carrier is configured to move from an initial position to a measuring position, the reaction carrier being located at a spaced location from the measuring system in the initial position, the reaction carrier being located adjacent to the measuring system in the measuring position.

12. A reaction carrier in accordance with claim 11, wherein the at least one flow channel is aligned with an inlet gas port and an outlet gas port of the measuring system when the reaction carrier is in the measuring position.

13. A measuring system for measuring a concentration of gaseous and/or aerosol components of a gas mixture, the system comprising:
a reaction carrier comprising at least one flow channel that forms a reaction chamber with a reactant, which is designed to react with at least one of the components to be measured in the gas mixture or with a reaction product of the component to be measured in an optically detectable manner and particles at least partially filling the flow channel the particles having a starting position before the gas mixture flows through the flow channel, and a flow position, wherein the particles are configured to move from the starting position to the flow position via the gas mixture flowing through the flow channel, wherein the particles in the starting position are optically distinguishable from the particles in the flow position; and
a measuring device comprising an optical sensor, which detects the flow channel of the reaction carrier and is configured to optically determine the starting position and the flow position of the particles.

14. A measuring system in accordance with claim 13, wherein at least one of the measuring device and the reaction carrier is configured to generate an electric or magnetic field in the flow channel of the reaction carrier.

15. A measuring system in accordance with claim 13, wherein the measuring device further comprises an analysis unit, the optical sensor recording a reference image of the flow channel before the delivery of the gas mixture through the at least one flow channel and the optical sensor recording a flow image of the flow channel during the delivery of the gas mixture through the at least flow channel, the analysis unit being configured to determine the gas mixture flowing through the flow channel based on the reference image and the flow image.

16. A measuring system in accordance with claim 13, wherein the reactant comprises a chemical compound, which reacts with the at least one of the components to be measured in the gas mixture or with the reaction product of the component to be measured upon the gas mixture being introduced into the at least one flow channel, the at least one of the components to be measured in the gas mixture being a gas component to be measured in the gas mixture, the reaction product of the component to be measured being an aerosol component.

17. A measuring method for measuring a concentration of gaseous and/or aerosol components of a gas mixture the method comprising the steps of:
providing a reaction carrier comprising at least one flow channel that forms a reaction chamber with a reactant, which is designed to react with at least one of the components to be measured in the gas mixture or with a reaction product of the component to be measured in an optically detectable manner and particles at least partially filling the flow channel the particles having a starting position before the gas mixture flows through the flow channel, and are brought by a gas flow through the flow channel into a flow position, wherein the particles are configured such that the particles in the starting position and the particles in the flow position can be optically distinguished and a measuring device comprising an optical sensor which detects the flow channel of the reaction carrier and is configured to optically determine the starting position and the flow position of the particles;
recording a reference image of the flow channel before a delivery of a gas flow through the flow channel, wherein the particles are in their starting position;
recording of a flow image of the flow channel during a delivery of gas flow through the flow channel; and
determining the gas flow flowing through the flow channel by the use of the reference image and the flow image.

18. A measuring method in accordance with claim 17, further comprising the method step of:
generating a restoring force during the delivery of the gas flow through the flow channel, which brings the particles into a restored position.

19. A measuring method in accordance with claim 18, further comprising the method step of:
dynamically modulating the restoring force during the delivery of the gas flow through the flow channel, so that the particles move to and fro between the restored position and the flow position or are held in a position between the restored position and the flow position.

20. An optical flow sensor for determining a flow of a fluid, the optical flow sensor comprising:
a transparent flow channel;
particles, the flow channel being at least partially filled with the particles, which have a flow shape, in order to be oriented into a flow position in a predetermined orientation in the direction of flow in a gas flow, and which possess mechanical, electric and/or magnetic properties in order to be brought into a restored position by a mechanical, electric and/or magnetic force acting on the particles, the particles being configured such that the particles in the restored position and the particles in the flow position can be optically distinguished;
a restoring device for generating the mechanical, electric and/or magnetic restoring force;
an optical sensor element, which is configured to detect a change in the positions of the particles from the starting position into the flow position; and
a control unit, which is configured to determine the flow of the fluid by means of the detected change in the positions of the particles.

\* \* \* \* \*